United States Patent [19]

Browning

[11] Patent Number: 4,948,580

[45] Date of Patent: Aug. 14, 1990

[54] MUCO-BIOADHESIVE COMPOSITION

[75] Inventor: Ivan Browning, Barnard Castle, England

[73] Assignee: E. R. Squibb & Sons, Inc., Princeton, N.J.

[21] Appl. No.: 281,416

[22] Filed: Dec. 8, 1988

[51] Int. Cl.$^5$ ............... A61K 31/74; A61K 9/06; A61K 6/00; A61F 13/02

[52] U.S. Cl. .................... 424/78; 424/434; 424/435; 424/443; 424/447; 424/448; 424/484; 514/944; 514/969

[58] Field of Search ............... 424/78, 434, 435, 436, 424/443, 447, 448, 484; 514/944, 969

[56] References Cited

U.S. PATENT DOCUMENTS

| | | |
|---|---|---|
| 3,029,187 | 4/1962 | Steinhardt et al. . |
| 3,029,188 | 4/1962 | Cyr et al. .............................. 424/83 |
| 3,312,594 | 4/1967 | Cyr et al. . |
| 3,984,571 | 10/1976 | Chen . |
| 4,292,972 | 10/1981 | Pawelchak et al. ................ 424/423 |
| 4,393,080 | 7/1983 | Pawelchak et al. .................. 524/17 |
| 4,540,602 | 9/1985 | Motoyama et al. . |
| 4,542,020 | 9/1985 | Jackson et al. . |
| 4,569,955 | 2/1986 | Dhabhar ............................. 523/120 |

OTHER PUBLICATIONS

Tsunenori et al., CA 104(10): 7507c.

*Primary Examiner*—Joseph L. Schofer
*Assistant Examiner*—Carmen Pili-Curtis
*Attorney, Agent, or Firm*—Burton Rodney

[57] ABSTRACT

A bioadhesive composition is provided which may be employed as an oral drug delivery system and includes a freeze-dried polymer mixture formed of the copolymer poly(methyl vinyl ether/maleic anhydride) and gelatin, which is dispersed in an ointment base such as mineral oil containing dispersed polyethylene. Such bioadhesive compositions may be used to deliver oral mucosa active ingredients such as steroids, anti-fungal agents, anti-bacterial agents and the like.

9 Claims, No Drawings

MUCO-BIOADHESIVE COMPOSITION

FIELD OF THE INVENTION

The present invention relates to a muco-bioadhesive composition which may be employed in an oral drug delivery formulation which muco-adhesive composition contains a freeze-dried combination formed of a lower alkyl vinyl ether/maleic anhydride copolymer or salt thereof and gelatin, dispersed in an ointment base.

BACKGROUND OF THE INVENTION

Drug delivery systems for delivering drugs to the oral mucosa include tinctures, buccal formulations and ointments. Tinctures are easily applied to oral lesions but may be ingested into the body within a relatively short time after application. Buccal formulations may be retained in the oral cavity for longer periods than tinctures; however, they are usually larger in size and thus uncomfortable to retain in the oral cavity and often cause tissue irritation. In addition, they may be separated from lesions by saliva or other exudate. Conventional ointment formulations may be readily applied. However, in many cases, they also may be readily removed from the oral cavity by mechanical movement of the oral tissue such as during speaking or eating. In addition, conventional ointments may bleed during storage or even after application. Moreover, bleeding of active ingredients from ointments after application to oral lesions may cause active ingredients to be separated from such lesions and carried by saliva to other locations in the oral cavity.

A discussion of prior art patents relating to various drug delivery systems including oral delivery systems and/or oral adhesives follows.

U.S. Pat. No. 3,029,187 to Steinhardt discloses anhydrous adhesive pharmaceutical vehicles specifically designed for adhering active ingredients to the oral mucosa which vehicles are formed of an intimate mixture of gelatin and a topically-acceptable vehicle such as petrolatum, lanolin, benzoinated lard, hydrogenated cotton seed oil, carboxymethyl cellulose, pectin, karaya gum, tragacanth, Irish moss extracts, alginates, polyvinyl pyrrolidone, carbo gum, guar gum and pre-treated water-soluble starch. Active ingredients which may be carried by such vehicles include antiseptics, anesthetics, steroids, hormones and antibiotics.

U.S. Pat. No. 3,029,188 to Cyr et al discloses gelatin oral adhesive pharmaceutical preparations which include an intimate admixture of particulate gelatin with mineral oil containing thickening agent, such as polyethylene, dispersed therein. Cyr et al indicate that portions of the gelatin may be substituted by other gums such as carboxymethyl cellulose, pectin, karaya gum, tragacanth, Irish moss extracts, alginates, polyvinyl pyrrolidone, carob gum, guar gum and pre-treated water-soluble starch.

U.S. Pat. No. 3,312,594 to Cyr et al discloses a long-lasting troche which contains a medicament and equal portions of pectin, gelatin and carboxymethylcellulose; the troche interacts with saliva to dissolve in the mouth to form an adhesive composition which secures and retains the medicament to the oral mucosa.

U.S. Pat. No. 3,984,571 to Chen discloses a liquid carrier for a diagnostic or therapeutic agent which liquid carrier includes a fine particle size hydrocolloid, such as a cellulose ether, suspended in a non-aqueous water-immiscible mobile liquid. When a composition containing the diagnostic or therapeutic agent in the liquid carrier is made to contact a moist surface, the mobile liquid is drained off and the hydrocolloid (carrying the diagnostic or therapeutic agent) attaches itself to the surface.

U.S. Pat. No. 4,542,020 to Jackson et al discloses antifungal suppository formulations which are substantially free of water which include an antifungal agent such as nystatin together with a hydrocolloid, such as sodium carboxymethyl cellulose or hydroxypropylmethyl cellulose and a low melting suppository base.

U.S. Pat. No. 4,540,602 to Motoyama Shimesu et al discloses a process for preparing a pharmaceutical composition containing a solid drug in the form of finely divided particles no greater than 10 microns in diameter, wherein a solid drug which is substantially water-insoluble is dissolved in a low-boiling hydrophobic organic solvent, the resulting solution is emulsified in water in the presence of a water-soluble high molecular weight substance which is hydroxypropyl cellulose, methyl cellulose, hydroxyethyl cellulose, hydroxypropyl methyl cellulose, hydroxypropyl ethyl cellulose, carboxymethyl cellulose sodium salt, alpha-starch, hydroxypropyl starch, pullulan, gum arabic, tragacanth gum, gelatin, polyvinyl alcohol, polyvinyl pyrrolidone and mixtures thereof and water is thereafter removed.

U.S. Pat. No. 4,569,955 to Dhabhar discloses a denture adhesive which is formed of an admixture of mixed partial salts of lower alkyl vinyl ether-maleic anhydride-type copolymers (such as the Ca/Na partial salt of methyl vinyl ether-maleic anhydride copolymer) with sodium carboxymethyl cellulose in a vehicle which is mineral oil thickened with polyethylene.

DESCRIPTION OF THE INVENTION

In accordance with the present invention, a long-lasting muco-bioadhesive ointment formulation is provided which has excellent bioadhesive properties, and upon absorption of water has excellent retention of water-soluble or water-insoluble medicament at a desired treatment site in the oral cavity. The bioadhesive ointment formulation of the invention is formed of a freeze-dried combination formed of a lower alkyl vinyl ether/maleic anhydride copolymer and gelatin, which hydrates, becomes adhesive and increases retention time of the medicament at the treatment site, and an ointment base composition, and optionally a water-soluble or water-insoluble therapeutically active ingredient or medicament.

It has been found that the freeze-dried combination of the lower alkyl vinyl ether/maleic anhydride copolymer and gelatin is a synergistic combination with respect to muco-adhesive properties so that the freeze-dried combination has enhanced muco-adhesive properties compared to a simple physical mixture of the copolymer and gelatin. Accordingly, the present invention includes the above freeze-dried combination as well.

The ointment formulation of the invention is easily applied and adheres to the membranes at the desired site and retains a uniform distribution of medicament at the desired site to provide long-lasting treatment.

The ointment formulation of the invention will include a freeze dried combination of a lower alkyl vinyl ether/maleic anhydride copolymer and gelatin in an amount within the range of from about 25 to about 75% by weight and preferably from about 35 to about 65% by weight, and an ointment base in an amount within the range of from about 75 to about 25% by weight and preferably from about 65 to about 35% by weight, and a water-soluble or water-insoluble medicament in an amount within the range of from about 0.01 to about 25% by weight, and preferably from about 0.05 to about 15% by weight, depending upon the particular medicament employed, all of the above % being based on the total weight of the ointment formulation.

The freeze-dried combination will include a weight ratio of lower alkyl vinyl ether/maleic anhydride copolymer to gelatin of within the range of from about 0.05:1 to about 1:1 and preferably from about 0.1:1 to about 0.5:1.

The lower alkyl vinyl ether/maleic anhydride copolymers suitable for use herein include poly(methyl vinyl ether/maleic anhydride) copolymer, or the mixed partial salts thereof such as the Ca:Na partial salt. These copolymers are known in the art and are disclosed, for example, in U.S. Pat. No. 4,569,955 and U.S. Pat. No. 3,003,988.

A preferred poly(methyl vinyl ether/maleic anhydride) copolymer is Gantrez AN (trademark of GAF Corp.).

The medicament which may be employed in the ointment formulation of the invention may be water-soluble or water-insoluble and may include antifungal agents, such as amphotericin B, nystatin, griseofulvin, miconazole, ketoconazole, tioconazole, econazole, clotrimazole, and other macrolide antifungal agents, antibacterials (such as metronidazole, penicillins, monobactams, ampicillin, neomycin, erythromycin, mupirocin, tyrothricin, gramicidin, cephalosporins, gentamycin and other aminoglycosides, anti-cancer agents (such as 5-fluorouracil), anti-inflammatory agents (such as hydrocortisone, other known steroids such as prednisone, prednisolone, triamcinolone, dexamethasone, and betamethasone), hormones (such as oestriol), analgesic and anti-inflammatory agents such as acetaminophen, phenacetin, aspirin, aminopyrine, sulpyrine, phenylbutazone, mefenamic acid, flufenamic acid, ibufenac, ibuprofen, indomethacin, colchicine, and probenecid, and anti-viral agents (such as acyclovir, ribavarin, trifluorothyridine or idoxuridine) antiseptics, hexachlorophene, tetramethyl thiuramdisulfide, benzalkonium chloride, thimerosal, hexylresorcinol, cresols, zinc oxide, methylene blue, boric acid, chloramine-T, gentian violet, phenyl mercuric chloride, phenyl mercuric nitrate basic, acriflavin, sodium perborate, metallic peroxides (e.g. sodium peroxide), sodium permanganate, and the halogens. The medicament will be present in an amount within the range of from about 0.01 to about 25% and preferably from about 0.05 to about 15% by weight depending upon the particular medicament employed and the desired site of action.

Ointment formulations containing such medicaments in accordance with the present invention may be administered up to two times per day or any convenient regimen.

The ointment base suitable for use herein may comprise any conventional ointment formulation suitable for use in the oral cavity, such as disclosed in Remington's "Pharmaceutical Sciences," Sixteenth Edition (Mack Publishing Co., Pa.). Preferred ointment base formulations are set out in U.S. Pat. Nos. 3,029,188 and 2,628,187 and comprise mineral oil containing a thickening agent, such as polyethylene, dispersed therein. The thickening agent will be present in an amount of from about 0.25 to about 50% of the combined weight of mineral oil and thickening agent.

The oils which may be used and which are embraced within the term "mineral oil" as used herein are the oils which are liquid at any temperature in the range from 0° C. to 60° C. and which are essentially hydrocarbons occurring in mineral oil, their distillates and their cracked or polymerized derivatives, an example of the last being polybutene which includes the polymers of butylene and its isomers. The mineral oil may be of any desired character or viscoity, from one which is a thin liquid to one which is so thick that it does not flow at ordinary temperature (20° C.).

Thickening (gelling) agents utilizable for dispersion in the mineral oil include, inter alia paraffin wax, amorphous wax (e.g. microcrystalline wax), ozokerite, animal waxes (e.g. beeswax), vegetable waxes (e.g. castor wax), and hydrocarbon polymers (e.g. polymers of ethylene having an average molecular weight varying from 3,500 to 26,000 and polyisobutylene of a high molecular weight). The preferred thickening agent is polyethylene having a molecular weight of at least 3,500.

A preferred ointment base formulation comprises mineral oil containing polyethylene having a molecular weight of at least 3,500. An example of such an ointment is Plastibase 50W (distributed by E. R. Squibb & Sons, Inc.).

Preferred ointment formulations of the invention are set out below.

| Ingredient | Mg/g · ointment formulation |
| --- | --- |
| Medicament (For example, triamcinolone acetonide) | 0.5 to 150 |
| Freeze-dried combination of poly(methyl vinyl ether/maleic anhydride) copolymer and gelatin (weight ratio of 0.1:1 to 0.5:1) | 350 to 650 |
| Ointment base, for example, Plastibase 50 W | 350 to 650 |

The ointment formulation of the invention may be prepared as follows.

The freeze-dried combination or complex of the lower alkyl vinyl ether/maleic anhydride copolymer and gelatin are prepared by mixing the two components together in a inert solvent such as water, water/ethyl alcohol mixture and the like at a temperature of from about 5 to about 50° C., until a substantially homogeneous mass is obtained and then freeze-drying the mass using conventional freeze-drying equipment such as an Edwards Mini Vac.

The ointment base, medicament and freeze-dried combination of the lower alkyl vinyl ether/maleic anhydride copolymer and gelatin blend are mixed, preferably under vacuum to prevent aeration, to form the ointment formulation of the invention.

The ointment formulations of the invention will be in the form of homogeneous pastes and will retain their homogeneity without bleeding and will remain flowable (that is, will not unduly harden) even upon prolonged storage or upon filling into tubes. Moreover, the oral formulations of the invention have excellent oral adhesiveness so that upon application to the oral cavity, the formulations are retained for prolonged periods, keeping their original shape at the site of application even after being heated by body temperature, and moistened with saliva. Accordingly, the oral formulations of the invention will maintain its pharmacological efficacy at the site of application without being transferred to other locations in the oral cavity.

The following working Examples represent preferred embodiments of the present invention. Unless otherwise indicated, all temperatures are expressed in degrees Centigrade.

EXAMPLE 1

A muco-adhesive formulation in accordance with the present invention and Control A having the following composition were prepared as described below.

A freeze-dried complex of the copolymer poly(methylvinyl ether/maleic anhydride) (Gantrez AN-169, trademark of GAF Corp.) and gelatin was prepared as follows.

100 g of gelatin (MW=100,000) was dissolved in 500g of hot (>60° C.) water using a Silverson homogenizer-mixer.

16.75 g of Gantrez AN-169 was dispersed in 67 g of cold water and the suspension heated to 95°-100° C. to form a viscous gel. A further 235 ml of water was added, with heating and stirring to produce a transparent, viscous solution. The Gantrez solution was poured into the gelatin solution with continuous mixing. A curdled mass formed which was dispersed by means of the Silverson mixer. A further 1 kg of cold water was added and the whole mixture stirred before the resultant slurry was poured into freeze drier trays. The product was processed through the freeze drier to produce a dry mass which was reduced to a powder in a hammer mill.

A blend of the above freeze-dried combination in Plastibase 50W ointment base were mixed together for 30 minutes at 40 rpm followed by 60 minutes at 25 rpm, under vacuum to prevent aeration, so that a homogeneous ointment was obtained. In Control A, a simple mixture of the Gantrez AN copolymer and gelatin were mixed with the Plastibase 50W ointment base as described above. The composition of each formulation is set out below in Table I.

TABLE 1

| Ingredient | Parts by Weight Example 1 | | Control A | |
|---|---|---|---|---|
| Poly(methyl vinyl ether/ maleic anhydride) | 7 | freeze dried mixture | 7 | simple physical mixture |
| Gelatin | 43 | | 43 | |
| Plastibase 50 W ointment [mineral oil-95% polyethylene-5% M.W. 21,000] | 50 | | 50 | |

Each of the ointment formulations (Example 1 and Control A) were evaluated for adhesion using the porcine model as described below.

Adhesion to mucosal tissue was measured using isolated pig cheek tissue. The test was performed using an Instron Universal tester. 2 mg of sample was placed on the lower tissue and wetted with 1.5 ul of distilled water to simulate the saliva. The upper tissue was lowered until it contacted the sample, a pressure of 0.4 g applied and allowed to stand in this condition for one minute. The crosshead was raised at 1 mm/minute and the tensile force recorded on the chart recorder. The peak tensile force was then determined from the trace.

As there was some cheek to cheek variation each sample was compared against a standard. At least five readings each of sample and standard were used to obtain an average value, each sample of tissue being used once only.

The results obtained show that the adhesion obtained using the Example 1 formulation of the invention (which included a freeze-dried or lyophilized complex of the poly(methyl vinyl ether/maleic anhydride)-copolymer and gelatin) was 667 mg force as opposed to an adhesion obtained with the Control A formulation (which included a simple physical mixture of the copolymer and gelatin) which was 517 mg force.

It is quite clear that there is a synergistic reaction with regard to adhesive properties between the copolymer and gelatin when the mixture is in freeze-dried form over the simple physical mixture of same.

EXAMPLES 2 AND 3

Oral steroid ointment formulations in accordance with the present invention having the following compositions are prepared as described below.

| Ingredient | Parts by Weight | |
|---|---|---|
| | Ex. 2 | Ex. 3 |
| Triamcinolone acetonide | 0.1 | 0.1 |
| Freeze-dried complex of poly(methyl vinyl ether/ maleic anhydride)(Gantrez AN) | 43 | 40 |
| Gelatin | 7 | 10 |
| Plastibase 50W ointment [mineral oil-95 polyethylene (M.W. 21,000) - 5%] | 59.9 | 54.9 |

The freeze-dried complex of the copolymer and gelatin prepared as described in Example 1 and ointment are mixed together for 30 minutes at 40 rpm followed by 60 minutes at 25 rpm, under vacuum to prevent aeration, until a substantially homogeneous ointment is obtained. Thereafter, triamcinolone acetonide is added with thorough mixing until a homogeneous ointment paste is obtained.

The so-formed oral steroid ointment formulations are found to have excellent bioadhesive properties.

What is claimed is:

1. An oral muco-bioadhesive composition comprising a mixture of (1) freeze dried combination comprising a lower alkyl vinyl ether/maleic anhydride copolymer or salt thereof and gelatin; and (2) an ointment therefor wherein the freeze dried product is present in an amount within the range of from about 25 to about 75% by weight of said composition and the ointment base is present in an amount within the range of from about 75 to about 25% by weight of the said composition.

2. The composition as defined in claim 1 wherein said ointment base is comprised of mineral oil thickened with polyethylene.

3. The composition as defined in claim 1 wherein the lower alkyl vinyl ether/maleic anhydride copolymer is employed in a weight ratio to the gelatin of within the range of from about 0.05:1 to about 1:1.

4. The composition as defined in claim 1 wherein the copolymer is poly(methyl vinyl ether/maleic anhydride).

5. The composition as defined in claim 4 wherein the copolymer is employed in a weight ratio to the gelatin of within the range of from about 0.05:1 to about 1:1.

6. The composition as defined in claim 5 wherein said freeze-dried combination comprises from about 35 to about 65% by weight of said composition and said ointment base comprises from about 65 to about 35% by weight of said composition.

7. The composition as defined in claim 6 wherein said copolymer is present in an weight ratio to said gelatin in the range of from about 0.1:1 to about 0.5:1 and said ointment base is mineral oil thickened with polyethylene and comprises from about 65 to about 35% by weight of said composition.

8. The composition as defined in claim 7 where said ointment base is comprised of mineral oil and polyethylene having a molecular weight of within the range of from about 3500 to about 26,000 in an amount within the range of from about 0.25 to about 50% by weight of said ointment base.

9. The composition as defined in claim 1 further including an oral mucosa active ingredient.

* * * * *